United States Patent [19]

Kato

[11] Patent Number: 4,896,963
[45] Date of Patent: Jan. 30, 1990

[54] AUTOMATIC ANALYZER

[75] Inventor: Yutaka Kato, Shizuoka, Japan

[73] Assignee: Olympus Optical Co., Ltd., Tokyo, Japan

[21] Appl. No.: 275,417

[22] Filed: Nov. 23, 1988

[30] Foreign Application Priority Data

Dec. 2, 1987 [JP] Japan .................................. 62-303207

[51] Int. Cl.$^4$ .......................... G01J 3/36; G01N 21/13
[52] U.S. Cl. ..................................... 356/328; 356/320; 356/414; 356/440; 422/64
[58] Field of Search ............... 356/320, 328, 409, 414, 356/419, 440; 422/64, 65

[56] References Cited

U.S. PATENT DOCUMENTS 4,762,420 8/1988 Bowley ............................. 422/65 X Primary Examiner—Vincent P. McGraw
Attorney, Agent, or Firm—Arnold, White & Durkee

[57] ABSTRACT

An automatic analyzer of a single-line and multi-item type having a circular reaction line along which a number of reaction vessels are transported in the stepwise manner, and a photometering apparatus in which white light is divided into a plurality of light beams having different wavelengths, by means of a diffraction grating, and the light beams are transmitted by means of light guides whose exit ends are arranged along the reaction line with a pitch which is different from that with which the reaction vessels are arranged. While the reaction vessels are moved by one pitch, a plurality of reaction vessels are photometered in time sequential manner.

8 Claims, 3 Drawing Sheets

FIG._1
*PRIOR ART*
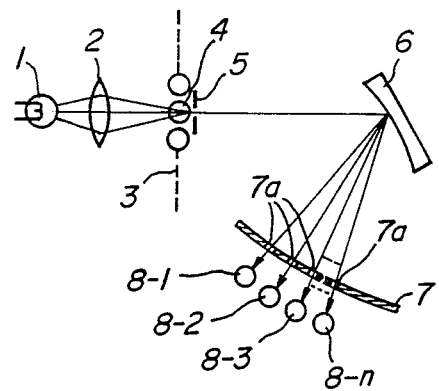
FIG._2
*PRIOR ART*
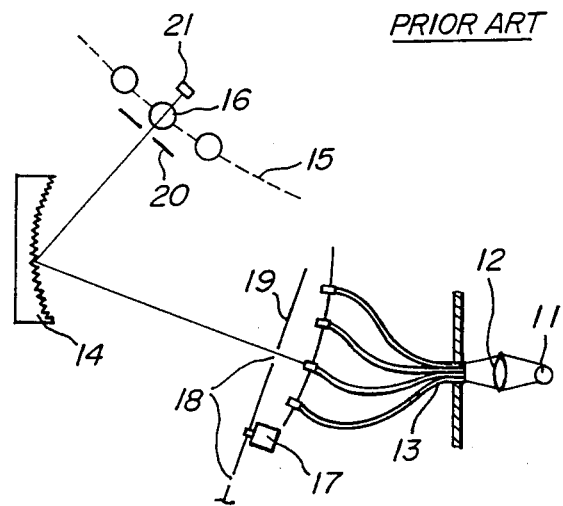

AUTOMATIC ANALYZER

BACKGROUND OF THE INVENTION

Field of the Invention and Related Art Statement

The present invention relates to an automatic analyzer comprising a reaction line along which a number of reaction vessels each containing respective test liquids are transported and photometering means for effecting the photometry for the test liquids in the reaction vessels by transmitting light beams through the reaction vessels.

An automatic analyzer of single-line and multi-item type has been proposed in which a plurality of test items, i.e. a plurality of substances in samples are analyzed by means of a single reaction line. In such an automatic analyzer, test liquids contained in reaction vessels have to be photometered with the aid of light beams having different wavelengths corresponding to respective test items.

FIG. 1 is a schematic view showing a known photometering apparatus disclosed in Japanese Patent Publication No. 65-21,303. The photometering apparatus comprises a light source 1 emitting white light, i.e. light including whole wavelength components, a condenser lens 2 for collecting the white light and making it incident upon reaction vessels 4 transported along a reaction line 3. Light transmitted through a test liquid contained in a reaction vessel 4 is made incident upon a spectroscope 6 via a slit 5 and is divided into a plurality of light beams having different wavelengths. These light beams are then made incident upon a plurality of light detectors 8-1, 8-2, ... 8-n, respectively by means of a slit 7 having a plurality of holes 7a. One or more output signals supplied from the light detectors 8-1, 8-2, ... 8-n are selected in accordance with test items to be measured for respective samples.

FIG. 2 is schematic view illustrating another known photometering apparatus described in Japanese Patent Laid-open Publication, Kokai Sho 60-117,118. In this known apparatus, white light emitted from a light source 11 is evenly made incident upon incident ends of a plurality of optical fibers 13 via a condenser lens 12. Exit ends of optical fibers 13 are secured at positions which are predetermined in accordance with wavelengths of measuring light beams emanating from a diffraction grating 14. In opposition to the exit ends of optical fibers 13 there is arranged a rotary disc 19 which is rotated by a motor 17. As shown in FIG. 3, the rotary disc 19 has formed therein a plurality of sector slits 18 corresponding to the positions at which the exit ends of optical fibers 13 are arranged. The motor 17 is driven such that any one of slits 18 in the disc 19 can be positioned opposite an exit end of an optical fiber in accordance with a test item destined for a test liquid contained in a reaction vessel 16 which is just indexed at a measuring position defined by slit 20. Therefore, a light beam having a desired wavelength is made incident upon the reaction vessel 16 from the diffraction grating 14, and the light transmitted through the reaction vessel is received by a light detector 21. The reaction vessels 16 are transported along a reaction line 15 through the measuring position.

In the known photometering apparatus illustrated in FIG. 1, since the white light has a large amount of energy and is made incident upon the test liquid, some substances in test liquids might be decomposed or altered, so that in practice it is difficult to carry out the measurement precisely.

This problem could be removed by the known apparatus illustrated in FIG. 2, because only a slight flux having a desired wavelength corresponding to a test item is made incident upon a test liquid. However, in this known apparatus, in order to select the wavelength it is necessary to rotate the slit disc 19, and therefore a long time period may be necessary for measuring test items, thereby reducing the processing ability of such systems. Moreover, the white light emitted from the light source 11 is divided into a plurality of light beams with the aid of the optical fibers and thus weaking the intensity of respective light beams. And as a result, noise can affect the weakened photometered signals thus decreasing the accuracy of the photometry.

U.S. Pat. No. 4,528,159, issued on July 9, 1985, discloses another known automatic analyzer comprising a light source emitting white light, first and second filter wheels arranged rotatably, and first and second light guides arranged between a cuvette and the filter wheels, respectively. Light emitted from the light source is evenly made incident upon filter elements of the first filter wheel, and a light flux emanating from a filter element is made incident upon a cuvette containing a test liquid via the first light guide. A light flux transmitted through the cuvette is made incident upon a light detector by means of the second light guide and a filter element of the second filter wheel. This known photometering apparatus is principally the same as the known apparatus shown in FIG. 2, and thus it requires a rather long time period to rotate the first and second filter wheels so as to index desired filter elements thereof into the measuring optical path in accordance with a test item to be measured.

SUMMARY OF THE INVENTION

The present invention provides a novel and useful automatic analyzer in which sample substances can be measured precisely without causing serious decomposition and alteration thereof and in which a number of samples can be processed efficiently.

According to the invention, an automatic analyzer comprises:

a reaction line;

means for transporting a number of reaction vessels arranged on the reaction line with a first pitch, said reaction vessels containing therein test liquids; and photometering means including a light source for emitting white light, means for dividing the white light into a plurality of light beams having different wavelengths, a plurality of light guides having incident ends each arranged to receive a respective one of said plurality of light beams and exit ends arranged along the reaction line with a second pitch which is different from said first pitch for projecting the light beams onto reaction vessels along measuring optical paths, and a plurality of light detectors each arranged on respective measuring optical paths to receive respective light beams emitted from the exit ends of respective light guides and transmitted through reaction vessels; whereby test liquids contained in a plurality of reaction vessels situating at the measuring optical paths are photometered with the aid of said plurality of light beams having different wavelengths in the time sequential manner, while the reaction vessels are moved along the reaction line over the first pitch.

DESCRIPTION OF THE DRAWINGS

FIG. 1 is a schematic view showing a known photometering apparatus;

FIG. 2 is a schematic view illustrating another known photometering apparatus;

DESCRIPTION OF THE PREFERRED EMBODIMENT

Figure 4:
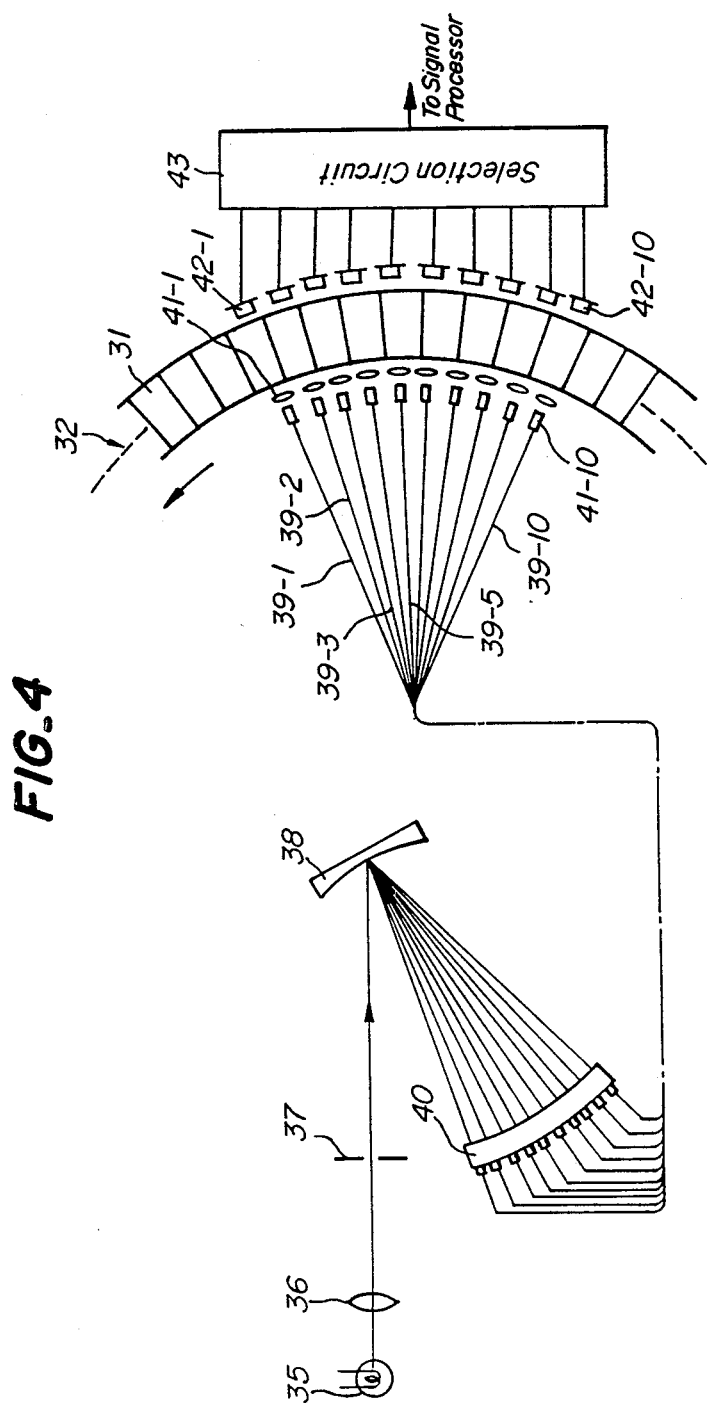
FIG. 4 is a schematic view showing an embodiment of the automatic analyzer according to the invention.

FIG. 4 is a schematic view showing an embodiment of the automatic analyzer according to the invention. A number of reaction vessels 31 are arranged on a circular reaction line 32 at a given first pitch and are transported in a stepwise manner pitch by pitch in a direction shown by an arrow A. In the present embodiment, a plurality of test items, i.e. plural kinds of sample substances can be measured with the aid of the single reaction line 32. To this end, while the reaction vessel array is moved over one pitch, a plurality of test liquids contained in reaction vessels 31 are measured with the aid of a plurality of light beams having different wavelengths in the time sequential manner, and while the reaction vessel array is in the stationary condition, various kinds of operations such as delivery of sample, delivery of first reagent, agitation, delivery of second reagent and washing are effected for reaction vessels situating at given positions.

The analyzer comprises a single light source 35 emitting white light. The white light emitted from the light source 35 is made incident via a condenser lens 36 and a slit 37 upon a diffraction grating 38 and is divided into a plurality of light beams having different wavelengths. In the present embodiment, there is produced ten light beams. These light beams are introduced into incident ends of light guides 39-1~39-10 each made of an optical fiber. The incident ends of light guides 39-1~39-10 are supported in position by means of a fitting member 40. Exit ends of the light guides 39-1~39-10 are arranged along an inner side of the reaction line 32 such that successive exit ends are separated from each other by a predetermined second pitch which is not equal to the first pitch of the reaction vessels. The light beams emanating from the exit ends of light guides 39-1~39-10 are projected onto reaction vessels on the reaction line 32 by means of lenses 41-1~41-10, respectively. Along the outer side of the reaction line 32 there are further arranged light detectors 42-1~42-10 at such positions that they are opposite to respective exit ends of light guides 39-1~39-10. Output signals from the light detectors 42-1~42-10 are supplied to a selection circuit 43 which selects one or more output signals which are then supplied to a signal processor not shown.

Figure 3:
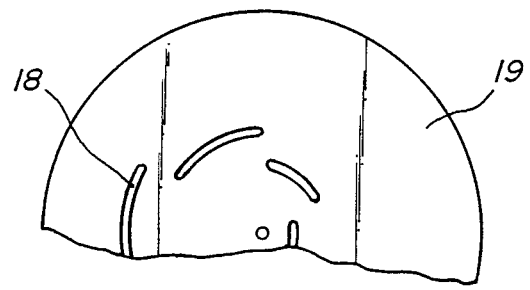
FIG. 3 is a plan view depicting a slit disc shown in FIG. 2.
Figure 5:
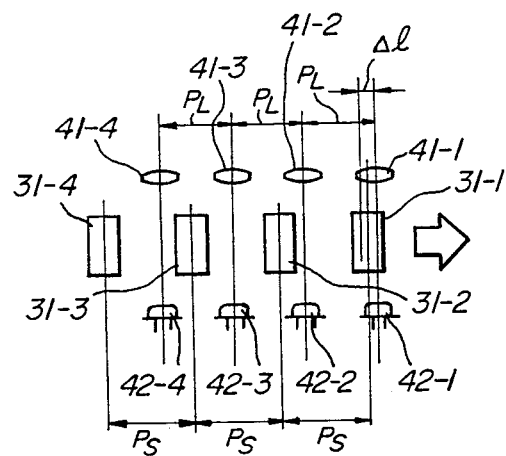
FIG. 5 is a schematic view representing the positional relationship between reaction vessel and photometering positions in the analyzer illustrated in FIG. 4.

FIG. 5 is a schematic view showing the positional relationship between the reaction vessels 31 and the measuring optical paths defined by the exit ends of light guides 39-1~39-10, lenses 41-1~41-10 and light detectors 42-1~42-10. In FIG. 5, only four reaction vessels 31-1~31-4 and four measuring optical paths defined by lenses 41-1~41-4 and light detectors 42-1~42-4 are illustrated for the sake of simplicity. The selection circuit 43 selects successively the output signals from the light detectors 42-1~42-10 and the signal processor samples an output signal measured for a test liquid and selected by the selection circuit at plural times to derive a plurality of sample values. Then, an average of these sample values is derived as a photometered value of the relevant test liquid.

Reaction vessels 31 are arranged with the first pitch $P_S$ and the measuring optical paths are separated by the second pitch $P_L$, so that the condition $P_S > P_L + \Delta l$ is satisfied, where $\Delta l$ is a distance of a central portion of the reaction vessel which has the uniform optical property and the measuring is effected while the light beam is transmitted through central portion having the distance $\Delta l$. At first, the photometry for the first reaction vessel 31-1 is completed while the reaction vessel array is moved over the distance $\Delta l$, and then the central portion of a second reaction vessel 31-2 moves into the measuring optical path defined by the next lens 41-2 and next light detector 42-2. While the reaction vessel array is then moved over the next distance $\Delta l$, the photometry for the second reaction vessel 31-2 is carried out. Similarly, the photometry for the successive reaction vessels 31-3~31-10 are effected each time the reaction vessel array is transported by the distance $\Delta l$. In this manner, when the reaction vessel array is moved over one pitch $P_S$, test liquids contained in the ten reaction vessels 31-1~31-10 are successively measured with the aid of the light beams having different wavelengths, and ten photometered values are obtained in the time sequential manner.

As explained above, according to this embodiment a plurality of test items are measured wth the aid of the single reaction line 32, so that test items to be effected for successive reaction vessels, i.e. the wavelengths of measuring light beams become random. Further, the photometry with a single wavelength and that with double wavelengths can be carried out at will. Therefore, in accordance with measuring information about the test item and the number of wavelengths which has been previously set, one or more output signals supplied from one or more light detectors defined by said measuring information are selected by the selector circuit 43, while the reaction vessel array is moved over the distance $\Delta l$. Then the selected output signal is sampled several times and an average of sample values is derived as a final photometered value.

In the present embodiment, ten reaction vessels are successively measured while the reaction vessel array is moved by one step, so that the requirement for the data processing can be mitigated and the sample processing ability can be improved in comparison with the known apparatus in which $P_S$ is set to be equal to $P_L$ and all the ten reaction vessels are measured simultaneously.

The present invention is not limited to the embodiment explained above, but many modifications and alternations may be conceived by those skilled in the art within the scope of the invention. In the above embodiment, the first pitch $P_S$ of the reaction vessels and the second pitch $P_L$ of the measuring optical paths, i.e. photometering positions are so set that $P_S > P_L + \Delta l$ is satisfied. However, they may be arranged to satisfy the condition $P_S < P_L - \Delta l$. Moreover, the photometering positions may be spread over the reaction line as long as the above mentioned conditions are satisfied. Further the reaction vessels may be measured every time they rotate by one revolution of the reaction line, or may be measured each time they rotate by a plurality of turns over the reaction line. In the above embodiment, the photometering is carried out always when the reaction vessel array is moved. However, if one or more reaction vessels situate at photometering positions while the reaction vessel array is in the stationary condition, the photometry may be carried out at such positions. Then, at the remaining photometering positions, the photometry may be effected while the reaction vessel array is rotated. It should be noted that the reaction vessel array may be moved continuously instead of intermittently. Further, the number of measuring wavelengths may be smaller or larger than ten. Finally although the present invention can be advantageously applied to the single-line and multi-item analyzer, the invention can be also applied to the analyzer in which a single test item is measured with the aid of two wavelengths, while the reaction vessels are transported along the single reaction line.

The merits of the present invention may be summarized as follows.

(1) The white light emitted from the light source is divided into a plurality of light beams having differet wavelengths, so that the test liquid is hardly decomposed and altered and the reliable measurement can be performed. Further, the measuring light beam has a relatively high intensity, stable data can be obtained without being affected by noise.

(2) The light beams having different wavelengths are always made incident upon the light detectors and it is not necessary to provide the optical and mechanical wavelength selecting means. Therefore, the wavelength selection time is not necessary, so that the data process can be carried out at a high speed.

(3) Since a plurality of photometered values are obtained in the time sequential manner, the requirement for the data process such as processing speed and data storing capacity can be mitigated.

(4) The layout and optical dimension of photometering system are set in accordance with the wavelength to be used, and thus it is possible to realize the ideal optical system easily. Moreover, since the white light is divided into several light beams having different wavelengths prior to transmitting the light with the aid of optical fibers, only a few light beams in the ultraviolet region may be transmitted by means of expensive quartz fibers, so that the whole optical system may be less expensive.

What is claimed is:
1. An automatic analyzer comprising
a reaction line;
means for transporting a number of reaction vessels arranged on the reaction line with a first pitch, said reaction vessels containing therein test liquids; and
photometering means including a light source for emitting white light, means for dividing the white light into a plurality of light beams having different wavelengths, a plurality of light guides each having incident ends arranged to receive a respective one of said plurality of light beams and exit ends arranged along the reaction line with a second pitch which is different from said first pitch for projecting the light beams onto reaction vessels along measuring optical paths, and a plurality of light detectors each arranged on respective measuring optical paths to receive respective light beams emitted from the exit ends of respective light guides and transmitted through reaction vessels; whereby test liquids contained in a plurality of reaction vessels situating at the measuring optical paths are photometered with the aid of said plurality of light beams having different wavelengths in a time sequential manner, while the reaction vessels are moved along the reaction line over the first pitch.

2. An automatic analyzer according to claim 1, wherein said first pitch $P_S$ with which the reaction vessels are arranged and said second pitch $P_L$ with which the exit ends of light guides are arranged satisfy the condition that $P_S > P_L + \Delta l$, wherein $\Delta l$ is a distance of a central portion of reaction vessel through which the photometering is effected.

3. An analyzer according to claim 2, wherein said reaction vessels are transported along the reaction line in a stepwise manner, and the photometering is effected while the reaction vessels are moved.

4. An analyzer according to claim 3, wherein said distance $\Delta l$ is determined such that when a central portion of a reaction vessel has just passed through a measuring optical path, a central portion of a next reaction vessel has just entered into a next measuring optical axis.

5. An analyzer according to claim 4, wherein said photometering means further comprises a selection circuit for selecting an output signal supplied from a light detector which receives a light beam transmitted through a central portion of reaction vessel.

6. An analyzer according to claim 1, wherein said means for dividing the white light into said plurality of light beams having different wavelengths comprises a diffraction grating, and each of said light guides is formed by an optical fiber.

7. An analyzer according to claim 6, wherein said reaction line is formed into a circular shape.

8. An automatic analyzer according to claim 1, wherein said first pitch $P_S$ with which the reaction vessels are arranged and said second pitch $P_L$ with which the exit ends of light guides are arranged satisfy the condition that $P_S < P_L - \Delta l$, wherein $\Delta l$ is a distance of a central portion of reaction vessel through which the photometering is effected.

* * * * *